United States Patent
Zhu et al.

(10) Patent No.: US 11,324,768 B2
(45) Date of Patent: May 10, 2022

(54) APPLICATIONS OF TRIACETYL-3-HYDROXYL PHENYL ADENOSINE IN TREATING VASCULAR INFLAMMATIONS OR IMPROVING VASCULAR ENDOTHELIUM FUNCTIONS

(71) Applicants: JIANGSU TASLY DIYI PHARMACEUTECAL CO., LTD., Jiangsu (CN); INSTITUTE OF MATERIA MEDICA, CHENESE ACADEMY OF MEDICAL SCIENCES, Beijing (CN)

(72) Inventors: Haibo Zhu, Beijing (CN); Minjie Wang, Beijing (CN)

(73) Assignees: JIANGSU TASLY DIYI PHARMACEUTICALS CO., LTD., Jiangsu (CN); INSTITUTE OF MATERIA MEDICA, CHINESE ACADEMY OF MEDICAL SCIENCES, Beijing (CN)

(*) Notice: Subject to any disclaimer, the term of this patent is extended or adjusted under 35 U.S.C. 154(b) by 391 days.

(21) Appl. No.: 16/303,739

(22) PCT Filed: May 23, 2017

(86) PCT No.: PCT/CN2017/085519
§ 371 (c)(1),
(2) Date: Nov. 21, 2018

(87) PCT Pub. No.: WO2017/202297
PCT Pub. Date: Nov. 30, 2017

(65) Prior Publication Data
US 2020/0316101 A1  Oct. 8, 2020

(30) Foreign Application Priority Data
May 24, 2016  (CN) .......................... 201610346541.9

(51) Int. Cl.
| | |
|---|---|
| A61K 31/7076 | (2006.01) |
| A61P 9/10 | (2006.01) |
| A61P 3/06 | (2006.01) |
| A61P 9/14 | (2006.01) |
| A61K 9/00 | (2006.01) |
| A61K 9/20 | (2006.01) |
| A61K 9/48 | (2006.01) |

(52) U.S. Cl.
CPC ............ *A61K 31/7076* (2013.01); *A61P 3/06* (2018.01); *A61P 9/10* (2018.01); *A61P 9/14* (2018.01); *A61K 9/0019* (2013.01); *A61K 9/20* (2013.01); *A61K 9/48* (2013.01)

(58) Field of Classification Search
CPC .......... A61K 31/7076; A61P 9/10; A61P 3/06; A61P 9/14
See application file for complete search history.

(56) References Cited

U.S. PATENT DOCUMENTS

| | | | |
|---|---|---|---|
| 8,435,962 B2 | 5/2013 | Zhu | |
| 10,293,043 B2* | 5/2019 | Mumm | ..................... A61P 1/16 |
| 2019/0070208 A1 | 3/2019 | Zhu et al. | |

FOREIGN PATENT DOCUMENTS

| | | |
|---|---|---|
| CN | 101874036 A | 10/2010 |
| CN | 102125580 A | 7/2011 |
| CN | 106573072 A | 4/2017 |
| JP | 2012519714 A | 8/2012 |
| JP | 2019510762 A | 4/2019 |
| RU | 2179021 C2 | 2/2002 |
| WO | 2015187295 A2 | 12/2015 |

OTHER PUBLICATIONS

Office Action with Search Report dated May 28, 2020. КИРЕЕВА В. В. и др. Дисфункция эндотелия как краеугольный камень сердечно - сосудистых событий молекулярно - и фармакогенетические аспекты//Российский | кардиологический журнал 2014, 10 (114): 64-68, [oh—лайн] [найдено May 18, 2020] найдено в Интернет На http://dx.doi.org/10.15829/1560 -4071-2014-10-64-68.

(Continued)

*Primary Examiner* — Lawrence E Crane
(74) *Attorney, Agent, or Firm* — Dilworth & Barrese, LLP

(57) ABSTRACT

There is provided herein a method of treating and/or alleviating vascular inflammation or vascular endothelial function disorders comprising administering 2',3,' 5'-triacetyl-N[6] (3-hydroxyphenyl)adenosine of formula (I):

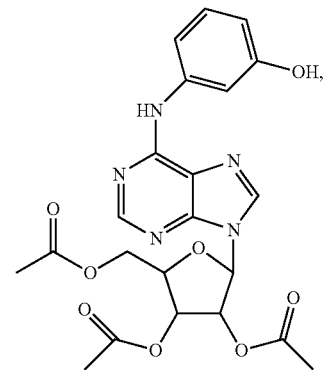

such as in the form of a pharmaceutical composition, to a person suffering from vascular inflammation or vascular endothelial function disorders.

5 Claims, 6 Drawing Sheets

(56) References Cited

OTHER PUBLICATIONS

Lian et al.; "A novel AMPK activator, WS070117, improves lipid metabolism discords in hamsters and HepG2 cells"; Lipids in Health and Disease (2011), 10:(6)7, pp. 1-8.

Jia et al.; "Simultaneous quantification of 2',3',5'-tri-0-acetyl-N6-(3-hydroxylaniline)adenosine and its principal metabolites in hamster blood by LC-MS/MS and its application in pharmacokinetics study"; J. Chromatogr. B 1022: (2016), 46-53.

Huang et al.; "Inhibition of ABCA1 protein degradation promotes HDL cholesterol efflux capacity and RCT and reduces atherosclerosis in mice"; Journal of Lipid Research vol. 56: (2015), p. 986-997.

Chen et al.; "AMP-activated protein kinase attenuates oxLDL uptake in macrophages through PP2A/NF-KB/LOX-1 pathway"; Vascular Pharmacology 85: (2016), p. 1-10.

Zhao et al.; "Triacetyl-3-hydroxyphenyladenosine, a derivative of cordycepin, attenuates atherosclerosis in apolipoprotein E-knockout mice"; Experimental Biology and Medicine, (2012), 237: p. 1262-1272.

Supplementary European Search Report from EP17802143.2 dated Dec. 16, 2019.

Li, Xiangping; "Dyslipidemia and Dysfunction of Vascular Endothelium"; Foreign Medical Sciences; 18(2): (1998).

International Search Report of PCT/CN/2017/085519 dated Aug. 24, 2017.

First Japanese Office Action in Japanese Application No. 2018-560192 dated Mar. 9, 2021.

Shrestha et al., "The effects of clopidogrel and fluoxetine on bleeding time and liver function alone and in combination"; Br J Clin Pharmacol, (2011) 73(6):, 1005-106.

He et al., "AMPK Suppresses Vascular Inflammation in Vivo by Inhibiting Signal Transducer and Activator of Transcription-1", Diabetes; (2015) 64:, 4285-4297.

Zhang et al., "Cordyceptin Inhibitors lipopolysaccharide (LPS)-Induced Tumor Necrosis Factort (TNF)-α Production via Activating AMP-Activated Protein Kinase (AMPK) Signaling"; Int. J. Mol. Sci.; (2014) 15: 12119-12134.

\* cited by examiner

APPLICATIONS OF TRIACETYL-3-HYDROXYL PHENYL ADENOSINE IN TREATING VASCULAR INFLAMMATIONS OR IMPROVING VASCULAR ENDOTHELIUM FUNCTIONS

CROSS-REFERENCE TO RELATED APPLICATIONS

This application claims priority to International PCT Application No. PCT/CN2017/085519 filed on May 23, 2017 which claims priority to Chinese Patent Application No. CN201610346541.9 filed on May 24, 2016.

FIELD OF THE INVENTION

The present invention relates to applications of 2',3,' 5'-triacetyl-N[6](3-hydroxyphenyl)adenosine and a pharmaceutical composition containing the same in the preparation of drugs for preventing and/or treating vascular inflammations or/and improving endothelial function disorders, belonging to the field of medicine and health.

BACKGROUND OF THE INVENTION

The occurrence and progression of cardiovascular diseases such as atherosclerosis, hypertension, and diabetes, etc. and the final damage of target organs are highly related to endovascular inflammations and endothelial dysfunction (ED). Endothelial cells regulate the maintenance of intravascular homeostasis by promoting vasodilatation, inhibiting smooth muscle proliferation, and inhibiting vascular inflammatory responses and a series of vascular protective effects. These effects are mainly affected by the endogenous vasodilator Nitric Oxide (NO). NO production disorders may lead to endothelial dysfunction, manifested as impaired endothelium-dependent relaxation. Improvement of vascular endothelial dysfunction is extremely important for the prevention and treatment of the occurrence and progression of atherosclerosis, hypertension, and diabetes. Clinical trials have shown that statins reduce the risk of coronary heart disease independently of their effects on blood lipids by improving endothelial dysfunction, both thiazolidinediones and angiotensin-converting enzyme inhibitors reduce the risk of cardiovascular disease by independent effect of improving endothelial dysfunction, therefore, it is very important to reduce vascular inflammations and improve endothelial dysfunction to reduce the risk of cardiovascular disease.

Currently, drugs that can improve the vascular endothelial function in the clinic mainly are statins, metformin, thiazolidinediones, and anti-hypertensive drugs such as angiotensin-converting enzyme inhibitors and other traditional cardiovascular disease treatment drugs, which mainly plays a role by increasing the activity of nitric oxide synthase and increasing NO production. However, myalgia and other adverse reactions caused by long-term use of statins make it difficult for patients to tolerate for a long time, biguanides may cause gastrointestinal disorders or occasionally cause lactic acidosis, and thiazolidine derivatives may cause serious side effects such as fluid overload or weight gain, liver function disorders, etc., thus they must be used with caution.

Triacetyl-3-hydroxyl phenyl adenosine (Patent No. ZL200980101131.6) is a new structural type compound with significant blood lipid regulating activity screened in cordycepin derivatives by the Institute of Materia Medica, Chinese Academy of Medical Sciences, and has the characteristics of small toxic and side effects, good pharmacokinetics, etc., and is currently in the preclinical research stage. At present, there is no report on the application of this compound in the reduction of vascular inflammations and increase of endothelial nitric oxide synthase activity to improve vascular endothelial dysfunction related diseases.

SUMMARY OF THE INVENTION

A technical problem to be solved by the present invention is to provide application of 2',3,' 5'-triacetyl-N[6](3-hydroxyphenyl)adenosine as shown in formula (I) in the preparation of drugs for preventing, alleviating or treating vascular inflammations or endothelial dysfunction.

In order to solve the technical problem of the present invention, the following technical solution is provided:

A first aspect of the technical solution of the present invention provides an application of 2',3,' 5'-triacetyl-N[6](3-hydroxyphenyl)adenosine as shown in formula (I) in the preparation of drugs for preventing and/or treating vascular inflammation,

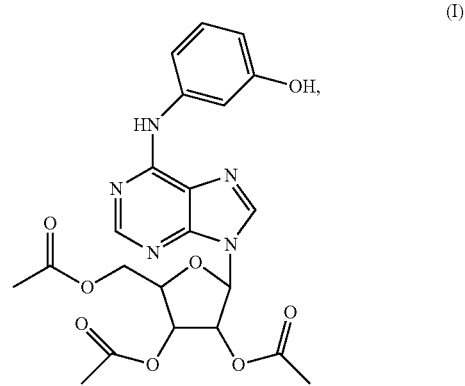

(I)

wherein, the vascular inflammations include acute vascular inflammations or chronic vascular inflammations; and the chronic vascular inflammations include vascular inflammations associated with hyperlipidemia.

A second aspect of the technical solution of the present invention provides an application of 2',3,' 5'-triacetyl-N[6](3-hydroxyphenyl)adenosine as shown in formula (I) in the preparation of drugs for preventing and/or treating vascular endothelial dysfunction,

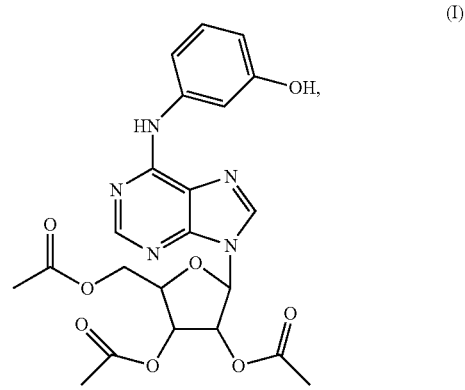

(I)

wherein, the vascular endothelial dysfunction include hyperlipidemia, atherosclerosis, hypertension, coronary heart disease, obesity, insulin resistance, or vascular endothelial dysfunction associated with type 2 diabetes.

The 2',3,' 5'-triacetyl-N'(3-hydroxyphenyl)adenosine of the present invention improves vascular endothelial nitric oxide synthase activity and increases NO production by inhibiting intravascular leukocyte-endothelial cells inflammatory response, thereby improving endothelial dysfunction and related diseases thereof.

A third aspect of the technical solution of the present invention provides an application of a pharmaceutical composition in the preparation of drugs for preventing, alleviating or treating vascular inflammations or endothelial dysfunction, characterized in that the pharmaceutical composition comprises 2',3,' 5'-triacetyl-N$^6$(3-hydroxyphenyl)adenosine of the formula (I) and a pharmaceutically acceptable carrier,

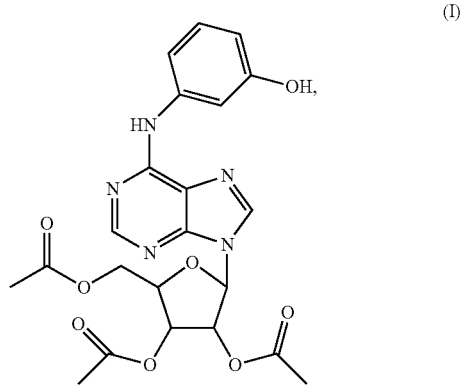

(I)

wherein, the vascular inflammations include acute vascular inflammations or chronic vascular inflammations; and the vascular endothelial dysfunction include hyperlipidemia, atherosclerosis, hypertension, coronary heart disease, obesity, insulin resistance, or vascular endothelial dysfunction associated with type 2 diabetes.

Further, the chronic vascular inflammations include vascular inflammations associated with hyperlipidemia.

The pharmaceutical composition can be prepared according to methods known in the art. Any dosage form suitable for human or animal use can be made by combining the compound of the present invention with one or more pharmaceutically acceptable solid or liquid excipients and/or auxiliaries. The content of the compound of the present invention in the pharmaceutical composition thereof is usually from 0.1 to 95% by weight.

The dosage form of the pharmaceutical composition of the present invention is tablets, capsules, pills, injections, sustained-release preparations, controlled-release preparations or various microparticle delivery systems.

Beneficial Technical Effect:

the 2',3,' 5'-triacetyl-N'(3-hydroxyphenyl)adenosine can reduce vascular inflammations and increase endothelial nitric oxide synthase activity, and improve vascular endothelial function disorders or its related diseases, this effect is independent of its lipid-lowering effect, ie, it has no correlation with the lipid-lowering effect of this compound.

DETAILED DESCRIPTION OF THE INVENTION

Figure 1:
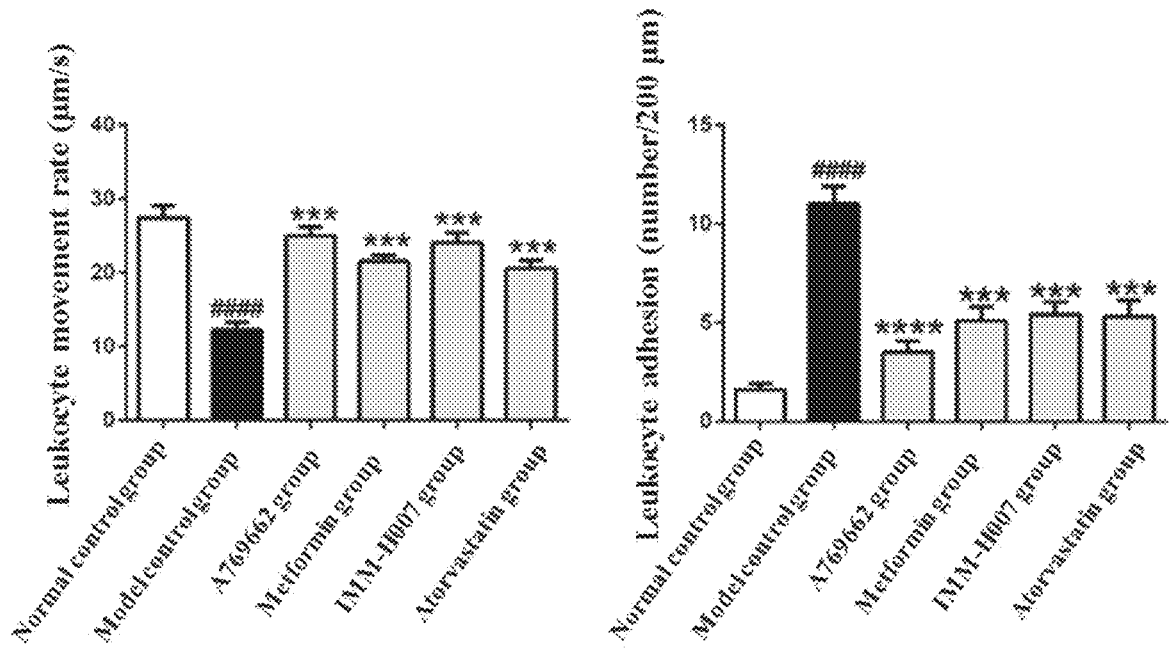
FIG. 1 illustrates that IMM-H007 inhibits TNF-α-induced acute intravascular inflammatory response in mice.

The following examples are used to further illustrate the present invention, but this does not mean any limitation to the present invention.

Example 1: 2',3,' 5'-triacetyl-N'(3-hydroxyphenyl) adenosine (IMM-H007) Inhibits Early Intravascular Inflammatory Response of Endothelial Dysfunction in Mice 1. IMM-H007 Inhibits TNF-α-Induced Acute Vascular Inflammations in Mice (Acute Inflammation Model)

Experimental Materials and Instruments

IMM-H007 (independently developed by the Institute of Materia Medica, Chinese Academy of Medical Sciences), metformin hydrochloride tablets (Sino-American Shanghai Squibb Pharmaceuticals Ltd.), A769662 (Shanghai Hanxiang Biological Technology Co., Ltd.), Murine TNF-α (Peprotech, INC), Rhodamine-6G (sigma), Pentobarbital Sodium (Serva), and sodium carboxymethyl cellulose (Sinopharm Chemical Reagent Co., Ltd.); Dynamic Visual Microvascular Research System (Gene&I-SMC1)

Animals and Experimental Design

SPF wild-type (WT) C57BL/6J mice (male, 6-8 weeks old, 18-20 g) were purchased from Beijing Huafukang Bioscience Co., Inc.

60 C57BL/6J mice were randomly divided into 6 groups according to body weight: normal control group, model control group, IMM-H007 group, positive control AMPK agonist group metformin, A769662 group, and atorvastatin group, respectively, and were intragastrically administered with physiological saline, IMM-H007 (100 mg/kg), metformin (260 mg/kg), and atorvastatin (lipitor, 10 mg/kg), respectively, and injected intraperitoneally with A769662 (30 mg/kg, which is difficult to absorb by oral administration) for 7 consecutive days. On the 8th day, except that the blank control group was intraperitoneally injected with normal saline, other groups were all intraperitoneally injected with TNF-α (0.3 μg/dose) to induce acute inflammations in the blood vessels. Four hours after the injection of TNF-α, the optic nerve vascular plexus was intravenously injected with 0.05% Rhodamine-6G, and leukocytes were fluorescently labeled with 100 μl. The mice were anesthetized with pentobarbital sodium. The right side of the mice was fixed on a observation table. A small mouth was cut along the abdominal cavity. The mesenteric vascular bed was gently pulled out. The small intestine of the mice was fixed in a observation window. The microscope is turned on to find a clear third-order mesenteric vein under a low power microscope, and then adjusted to 20-fold magnification for observation, after adjusting the brightness and focal length to the optimum, the white light was turned off, the fluorescence was turned on, and a 1 min leukocyte movement video was collected from each vessel segment using the ToumView software of the Dynamic Visual Microvascular Research System (Gene&I-SMC1). The leukocyte movement rate and leukocyte-endothelial cell adhesion number reflect intravascular inflammations and are early signs of endothelial dysfunction.

Detection Indicators (1) leukocyte movement rate (decrease in leukocyte movement rate, reflects the occurrence of inflammatory response in the blood vessel, changes of leukocyte movement rate after administration of the drugs were observed to reflect the inhibitory effect of the drugs on the inflammatory response.): Three mesenteric venules were observed in each mouse. The leukocyte movement rate was analyzed with image pro 6.0. At least three observation points were selected for each observation field, and at least 9 observation sites were finally counted for each mouse. The mean value was calculated to obtain the average leukocyte movement rate.

and (2) Number of leukocyte-endothelial cell adhesion (increased number of leukocyte adhesion reflects an increase in intravascular inflammatory response, which may cause endothelial dysfunction): the number of leukocyte adhesion was observed for each blood vessel at 200 μm (adhesion to endothelial cells without movement within 30 seconds, ie. adhesion).

Data Statistics

Experimental results were expressed as mean X±SD. A t-student test was performed using Graphpad Prism software. Differences between groups were analyzed by one way-ANOVA parameter analysis or non-parametric LSD-t method. $P<0.05$ indicated a statistical difference, and $P<0.01$ indicated a significant difference.

Experimental Results

The inflammatory factors, such as TNF-α, cause the slowing of the leukocyte movement rate, the increase in number of leukocyte-endothelial cell adhesion is an important cause of endothelial dysfunction, and endothelial dysfunction can aggravate vascular injury. The results showed that intravascular acute inflammations occurred after intraperitoneal injection of TNF-α (0.3 μg/dose) for 4 hours compared with the normal control group, and the leukocyte movement rate was decreased and the number of leukocyte adhesion was increased in the model control group. After administration of IMM-H007 (100 mg/kg), compared with the model control group, the leukocyte movement rate was significantly increased and the number of endothelial cell adhesion was significantly decreased, indicating that IMM-H007 can reduce the intravascular inflammatory response induced by the inflammatory factor TNF-α (results are shown in Table 1 and FIG. 1).

TABLE 1

IMM-H007 Inhibits TNF-α-Induced Acute Intravascular Inflammatory Response in Mice

| Groups | N | Dose | Leukocyte movement rate (microns/second) | Number of leukocyte adhesion (number/200 micron) |
|---|---|---|---|---|
| Normal control group | 10 | — | 27.4 ± 5.2 | 1.6 ± 0.9 |
| Model control group | 10 | — | 12.22 ± 3.2#### | 11 ± 2.7#### |
| IMM-H007 | 10 | 100 mg/kg | 24.1 ± 4.2*** | 5.4 ± 2.0*** |
| A769662 | 10 | 30 mg/kg, ip | 24.9 ± 3.8*** | 3.5 ± 1.8**** |
| Melbine | 10 | 260 mg/kg | 21.5 + 2.5*** | 5.1 ± 2.2*** |
| Atorvastatin | 10 | 10 mg/kg | 20.6 + 3.3*** | 5.3 + 2.6*** |

$P < 0.0001$ compared with normal control group;
***$P < 0.001$,
****$P < 0.0001$ compared with model control group 2. IMM-H007 Inhibits Intravascular Inflammatory Response in High-Fat-Fed ApoE−/− Mice (Chronic Inflammation Model)

Experimental Materials and Instruments

IMM-H007 (independently developed by the Institute of Materia Medica, Chinese Academy of Medical Sciences), metformin hydrochloride tablets (Sino-American Shanghai Squibb Pharmaceuticals Ltd.), A769662 (Shanghai Hanxiang Biological Technology Co., Ltd.), Rhodamine-6G (sigma), Pentobarbital Sodium (Serva), sodium carboxymethyl cellulose (Sinopharm Chemical Reagent Co., Ltd.), Mouse TNF-α ELISA Kit (Andy gene), and Mouse VCAM-1 ELISA Kit (Andy gene); Dynamic Visual Microvascular Research System (Gene&I-SMC1), and BioTeK Epoch reader.

Animals and Experimental Design

ApoE−/− mice with C57BL/6 background (male, 6-8 weeks old, 18-20 g) and C57BL/6 mice were purchased from the Institute of Laboratory Animal Sciences, Chinese Academy of Medical Sciences (Beijing Huafukang Bioscience Co., Inc.).

After 1 week of adaptive feeding, the animals were randomly divided into 4 groups according to body weight: model control group, A769662 (30 mg/kg, ip), metformin (260 mg/kg), IMM-H007 (100 mg/kg) administration groups, 7 in each group, and were given a high-fat diet (78.6% basal diet, 10% lard, 1.00%/cholesterol, 10% egg yolk powder, and 0.4% bile salt), and simultaneously administered intragastrically at a dose of 0.1 ml/10 g body weight, and were continuously administered and fed for 8 weeks. The mice were anesthetized with pentobarbital sodium (60 mg/kg body weight). The right side of the mice was fixed on a observation table. A small mouth was cut along the abdominal cavity. The mesenteric vascular bed was gently pulled out. The small intestine of the mice was fixed in an observation window, the microscope is turned on to find a clear third-order mesenteric vein under a low power microscope, and then adjusted to 20-fold magnification for observation, after adjusting the brightness and focal length to the optimum, the white light was turned off, the fluorescence was turned on, and the leukocyte movement in the blood vessel could be observed. A 1 min leukocyte movement video was collected from each vessel segment using the ToumView software of the Dynamic Visual Microvascular Research System (Gene&I-SMC1). Leukocyte movement rate and number of leukocyte-endothelial cells adhesion were analyzed using image pro 6.0.

Detection Indicators (1) Leukocyte Movement Rate and (2) Number of Leukocyte-Endothelial Cell Adhesion Data Statistics Experimental results were expressed as mean X±SD. A t-student test was performed using Graphpad Prism software. Differences between groups were analyzed by one way-ANOVA parameter analysis or non-parametric LSD-t method. P<0.05 indicated a statistical difference, and P<0.01 indicated a significant difference.

Experimental Results

Figure 2:
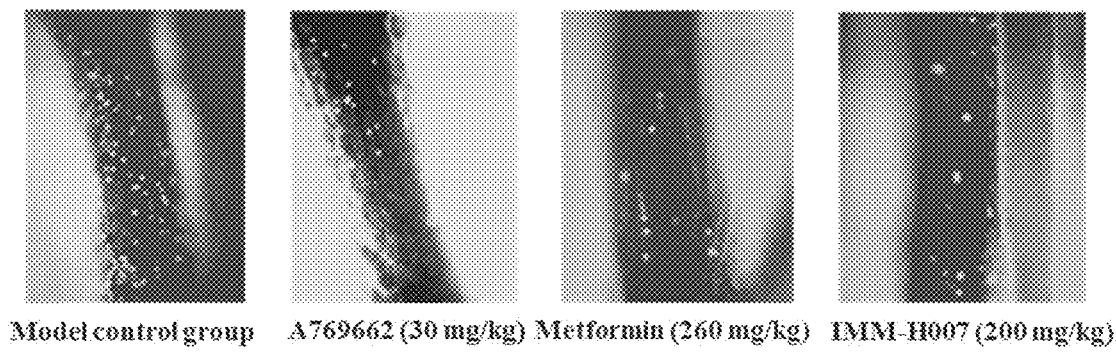
FIG. 2 illustrates that IMM-H007 alleviates vascular inflammatory response in high-fat-fed ApoE−/− mice.
Figure 2:
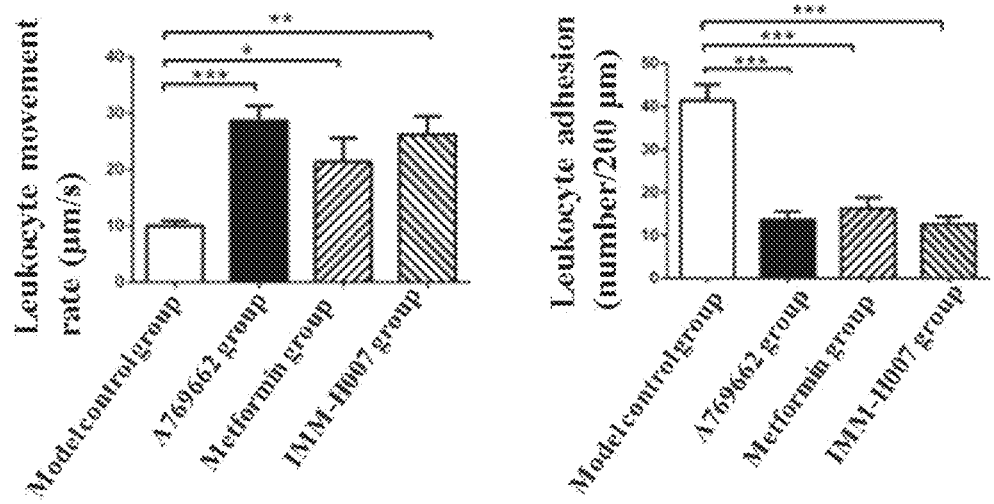

A high-fat diet increases the low-density lipoprotein cholesterol in the blood and stimulates endothelial cells to cause an inflammatory response that leads to slower leukocyte movement rate and increased number of leukocyte-endothelial cell adhesion, and causes endothelial function disorders, which in turn may lead to the occurrence of atherosclerosis. After administration of IMM-H007 (100 mg/kg), compared with the model control group, leukocyte movement rate was significantly increased and number of endothelial cell adhesion was significantly reduced, indicating that IMM-H007 significantly inhibits the leukocyte-endothelial cell inflammatory response in high-fat-fed ApoE−/− mice and reduces vascular inflammations induced by high-fat (results are shown in Table 2 and FIG. 2).

TABLE 2

IMM-H007 Reduces Vascular Inflammatory Response in High-fat Fed ApoE−/− Mice

| Groups | N | Dose | Leukocyte movement rate (microns/second) | Number of leukocyte adhesion (number/200 micron) |
|---|---|---|---|---|
| Model control group | 7 | — | 9.99 ± 2.3 | 41.4 ± 9.8 |
| IMM-H007 | 7 | 100 mg/kg | 26.2 ± 8.7* | 12.5 ± 4.9*** |
| A769662 | 7 | 30 mg/kg, ip | 28.7 ± 7.0*** | 13.7 ± 4.9*** |
| Metformin | 7 | 260 mg/kg | 21.4 + 11.0** | 16.3 ± 6.8*** |

*P < 0.05,
**P < 0.01,
***P < 0.001 compared with model control group

Example 2: 2',3,' 5'-triacetyl-$N^6$(3-hydroxyphenyl) adenosine (IMM-H007) Improves Vascular Endothelial Function Experimental Materials and Instruments IMM-H007 (independently developed by the Institute of Materia Medica, Chinese Academy of Medical Sciences), A769662 (Shanghai Hanxiang Biological Technology Co., Ltd.), metformin hydrochloride tablets (Sino-American Shanghai Squibb Pharmaceuticals Ltd.), Pentobarbital Sodium (Serva), sodium carboxymethyl cellulose (Sinopharm Chemical Reagent Co., Ltd.), sodium chloride, potassium chloride, magnesium sulfate, sodium bicarbonate, glucose, EDTA, and acetylcholine (sigma), sodium nitroprusside (VETEC), R-(−)phenylephrine (J&K Scientific LTD.), Mouse TNF-α ELISA Kit (Andy gene), Mouse VCAM-1 ELISA Kit (Andy gene), Triglyceride Assay Kit, Total Cholesterol Assay Kit, High-Density Lipoprotein Cholesterol Assay Kit, and Low-Density Lipoprotein Cholesterol Assay Kit (BioSino Bio-Technology & Science Inc.), and Free fatty Acid Assay Kit (Sekisui Medical Technology LTD.); analytical balance, Olympus SZ51 stereomicroscope, shaker, stapler, Pressure Myography System-120CP, fine microsurgery tweezer, fine microsurgical scissor, 95% $O_2$ and 5% $CO_2$ mixture, and surgical operation silicone disk.

Animals and Experimental Design

ApoE−/− mice with C57BL/6 background (male, 6-8 weeks old, 18-20 g) and C57BL/6 mice were purchased from Beijing Huafukang Bioscience Co., Inc.

After 1 week of adaptive feeding, the animals were randomly divided into 7 groups according to body weight: normal control group, model control group A769662 (30 mg/kg) administration group, metformin (260 mg/kg) administration group, IMM-H007 low, medium, and high administration groups (50, 100, 200 mg/kg), 8 in each group, and were given a high-fat diet (78.6% basal diet, 10% lard, 1.0% cholesterol, 10% egg yolk powder, and 0.4% bile salt), and simultaneously administered intragastrically at a dose of 0.1 ml/10 g body weight, and were continuously administered and fed for 8 weeks to establish an atherosclerosis model.

Detection Indicators (1) Effect of IMM-H007 on Blood Lipid Levels in ApoE−/− Mice: Total Cholesterol (TC), Triglyceride (TG), Low-Density Lipoprotein Cholesterol (LDL), High-Density Lipoprotein Cholesterol (HDL), and Free Fatty Acid (FFA)

Operated according to kit instructions (2) Effect of IMM-H007 on Serum Inflammatory Factors TNF-α and VCAM-1 in ApoE−/− Mice Operated according to kit instructions (3) Effect of IMM-H007 on Mesenteric Microvascular Endothelial Function in ApoE−/− Mice PSS and KPSS solutions were configured according to the instructions and used at the same time of the day. The PSS solution was taken out before the start of the experiment and pre-oxygenated for about 20 min. The ApoE−/− mice, which were fed with high-fat and simultaneously administered for 10 weeks, were anesthetized with pentobarbital sodium. The mice were supine and fixed. The abdominal cavity was opened along the median line. The mesenteric vascular bed was isolated and placed in the pre-oxygenated 20-minute PSS buffer. Under a stereomicroscope, a third-order mesenteric artery with a length of about 3 mm was carefully isolated. Firstly, the blood vessel was fixed to a P1 glass cannula and the coil was tightened. Note: the proximal end should be connected to the P1 end, and the P2 end vessel should be fixed and the coil should be tightened. The Chamber was placed on a objective table of the microscope and the data connection between Chamber and Interface was checked. The bath cover was covered and the oxygen was introduced, to exhaust air in the pipeline. The blood vessel image was found under the microscope and then the microscope was turned to camera mode. (The knob on the side of the eyepiece was rotated to graph.) MyoVIEW software was opened. The Camera window Capture was clicked to display the blood vessel image. The equilibration of blood vessels slowly rose from 10 mmHg to 60 mmHg, and each step was 300 s. After the equilibration procedure was completed, the solution in the bath was drained. Blood vessels were stimulated (10 ml) for 2 min using a 37° C. pre-heated KPSS solution, and changes in vasoconstriction were observed, and the blood vessels were then eluted using the PSS solution to baseline. The blood vessels were equilibrated at 60 mmHg 37° C. for 45 minutes, during which time the fluid was replaced every 20 minutes. The experiment was started: observing the vasodilatory response induced by $10^{-10}$ to $10^{-5}$ M Ach after pre-contraction with 2 μM phenylephrine, to evaluate the effect of the drugs on the vascular endothelial function. At the end of the experiment, the fresh 37° C. pre-heated PSS buffer was replaced for equilibration for 30 min, and the $10^{-10}$M to $10^{-3}$ M sodium nitroprusside were given to induce vasodilatory response after pre-contraction with 2 μM phenylephrine, to evaluate the effect of the drugs on vascular smooth muscle function. $LD_1$ was the diameter of blood vessel after relaxation by administration of different concentrations of ACh or sodium nitroprusside, $LD_2$ was the diameter of blood vessels after pre-contraction with phenylephrine, and $LD_3$ represented the maximum diastolic diameter of blood vessel without any stimulant.

The relaxation response to Ach and sodium nitroprusside after pre-contraction with phenylephrine was expressed as the percentage increase in the vascular diameter: % Relaxation=$(LD_1-LD_2)/(LD_3-LD_2)\times 100$.

(4) Effect of IMM-H007 on Endothelial Function of Thoracic Aorta in ApoE−/− Mice The mice were anesthetized. The thoracic aorta was quickly taken, after carefully stripping the surrounding tissue, was cut into a vascular ring with a length of about 3 mm. The vascular ring was carefully hung on a tonotransducer, given an initial tension of 0.5 g and equilibrated for 90 minutes or more. During the equilibration process, the fluid was replaced every 20 minutes, aeration was maintained and the temperature was maintained at 37° C. The vascular ring was equilibrated for about 1 hour and stimulated twice with saturated KCl (60 mM) to detect whether the blood vessel was active. After vasoconstriction was stabilized, KCl was washed away immediately. After the last replacement of the fluid, the vascular ring was equilibrated for 20 minutes, given phenylephrine 1 μM to stimulate vasoconstriction, and after vasoconstriction was stabilized, it was cumulatively administered with acetylcholine (Ach, $1\times10^{-10}$ to $1\times10^{-1}$) and sodium nitroprusside (SNP, $10^{-10}$ to $10^{-4}$ M) to record the vasodilation curve.

Vasodilation rate=[PE-induced vascular tone (g)-vascular tension after addition of ACh (g)]+[PE contraction-induced tension (g)-basal vascular tone (g)]×100%.

(5) Discussion of the Mechanism of IMM-H007 in Improving Endothelial Function

The expression levels of AMPK, pAMPK, peNOS, eNOS, Caveolin-1 proteins were analyzed and measured by Western Blotting to determine the total nitric oxide synthase activity in serum.

(6) Effect of IMM-H007 on Plaque Area in ApoE−/− Mice

The aortic root was stained with oil red O and the overall length of the aorta was stained with oil red O. The pathological images were analyzed by Photoshop, Image 1, and Image-Pro Plus softwares. The pathological grading data were statistically analyzed using Chi-square test. After comparison, P< 0.05, P< 0.01 showed a statistical difference.

Data Statistics

Experimental results were expressed as mean X±SD. A t-student test was performed using Graphpad Prism software. Differences between groups were analyzed by one way-ANOVA parameter analysis or non-parametric LSD-t method. P<0.05 indicated statistical difference, and P<0.01 indicated significant difference.

Figure 3:
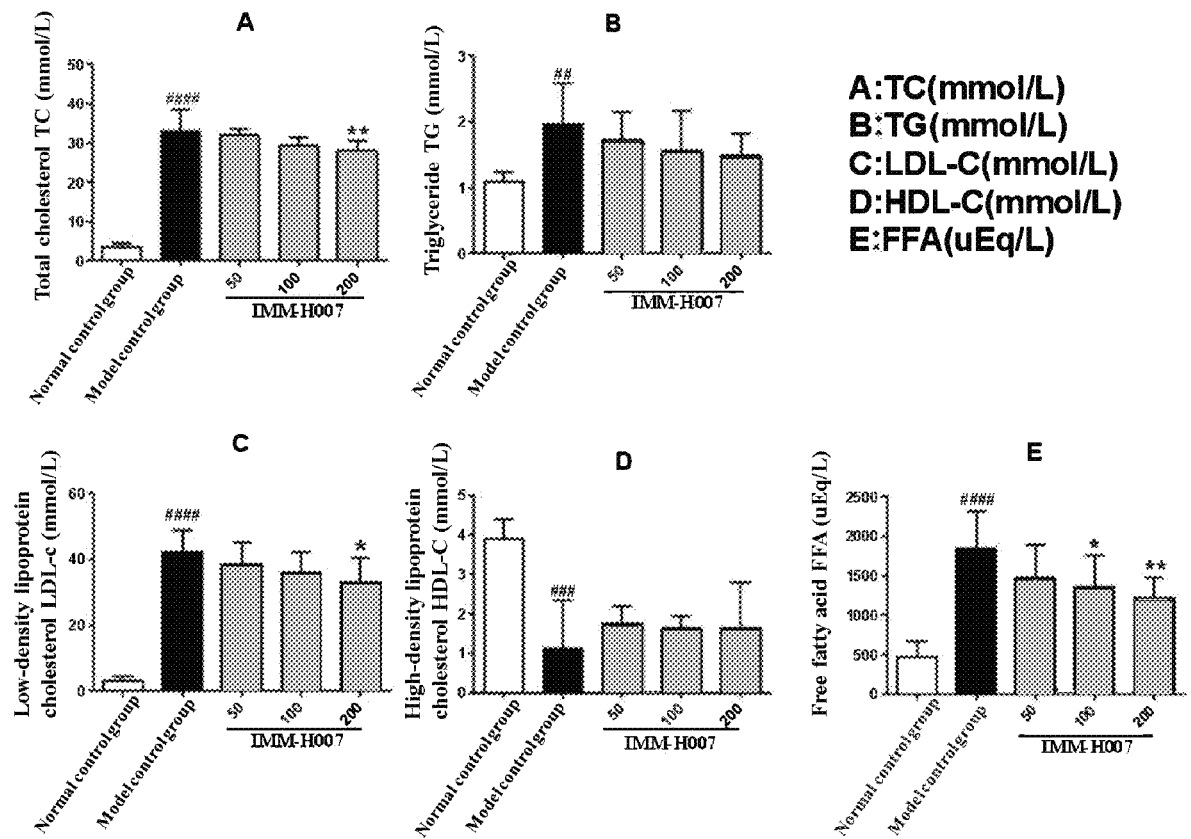
FIG. 3 illustrates effect of IMM-H007 on blood lipid levels in ApoE−/− mice.

Experimental Results (1) Effect of IMM-H007 on Blood Lipid Levels in ApoE−/− Mice The results showed that after 8 weeks of feeding with high-fat diet, the total cholesterol, triglyceride, low-density lipoprotein cholesterol and free fatty acid were increased and the high-density lipoprotein cholesterol was decreased in the model control group compared with the normal control group. The IMM-H007 administration 50 mg/kg dose group had no effect on total cholesterol, triglyceride, low-density lipoprotein cholesterol, free fatty acid, and high-density lipoprotein cholesterol; the IMM-H007 administration 100 mg/kg dose group had no effect on cholesterol, triglyceride, low-density lipoprotein cholesterol, and high-density lipoprotein cholesterol, and decreased free fatty acid to some extent; and in the IMM-H007 administration 200 mg/kg dose group, total cholesterol, low-density lipoprotein, and free fatty acid were decreased compared to the model control group (results are shown in Table 3 and FIG. 3).

TABLE 3

Effect of IMM-H007 on Blood Lipid Levels in ApoE−/− mice

| Groups | N | Dose | Total cholesterol (TC) | Triglyceride (TG) | Low-density lipoprotein (LDL-C) | High-density lipoprotein (HDL-C) | Free fatty acid (FFA) |
|---|---|---|---|---|---|---|---|
| Normal control group | 8 | — | 3.59 ± 0.78 | 1.1 ± 0.1 | 2.95 ± 1.47 | 3.92 ± 0.46 | 470 ± 201 |
| Model control group | 8 | 30 mg/kg, ip | 33.03 ± 5.43#### | 1.9 ± 0.62## | 42.37 ± 6.49## | 1.13 ± 1.21 | 1853 ± 474.8#### |
| IMM-H007 | 8 | 50 mg/kg | 31.92 ± 1.72 | 1.73 ± 0.42 | 38.63 ± 6.42 | 1.77 ± 0.42 | 1477 ± 423 |
| IMM-H007 | 8 | 100 mg/kg | 29.21 ± 2.36 | 1.56 ± 0.59 | 36.16 ± 6.08 | 1.63 ± 0.33 | 1356 ± 401* |
| IMM-H007 | 8 | 200 mg/kg | 28.00 ± 2.62** | 1.48 ± 0.34 | 33.21 ± 7.36* | 1.64 ± 1.15 | 1225 ± 251** |

Figure 4:
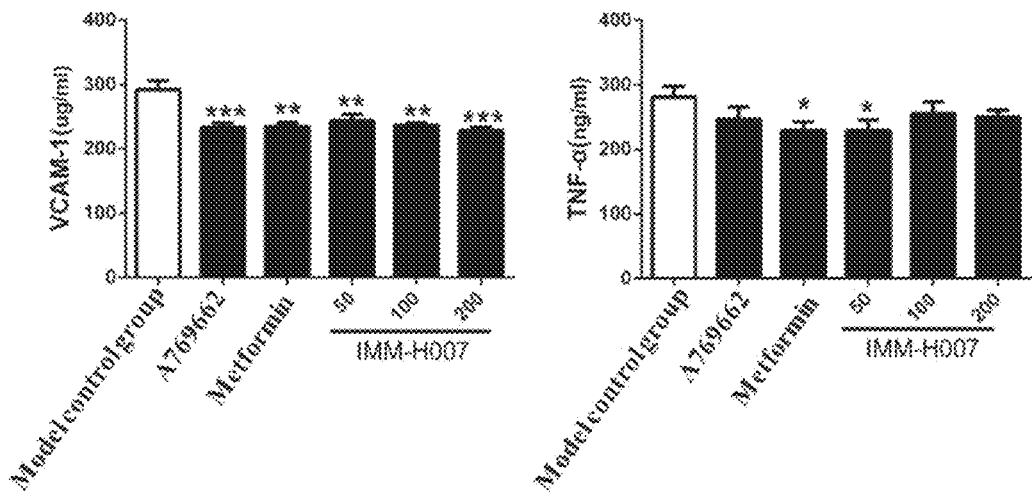
FIG. 4 illustrates effect of IMM-H007 on serum inflammatory factors TNF-α and VCAM-1 in ApoE−/− mice.

P < 0.05,

P < 0.01,

P < 0.001,

<0.0001 compared with normal control group;

*P < 0.05,

**P < 0.01,

***P < 0.001 compared with model control group (2) Effect of IMM-H007 on Serum Inflammatory Factors TNF-α and VCAM-1 in ApoE−/− Mice The results showed that compared with the model control group, IMM-H007 at a dose of 50, 100, or 200 mg/kg could reduce the serum VCAM-1 level in ApoE−/− mice, and IMM-H007 at a dose of 50 mg/kg reduced the expression of serum TNF-α in ApoE−/− mice, indicating that administration of IMM-H007 can reduce the levels of related inflammatory factors in serum (results are shown in Table 4 and FIG. 4).

TABLE 4

Effect of IMM-H007 on serum inflammatory factors TNF-α and VCAM-1 in ApoE−/− mice

| Groups | N | Dose | VCAM-1 | TNF-α |
|---|---|---|---|---|
| Model control group | 7 | — | 292.5 ± 37.2 | 281.3 ± 43.6 |
| A769662 | 7 | 30 mg/kg, ip | 233.1 ± 18.3*** | 247.3 ± 49.7 |
| Metformin | 7 | 260 mg/kg | 234.9 ± 16.7** | 229.1 ± 35.2*** |
| IMM-H007 | 7 | 50 mg/kg | 243.6 ± 26.2** | 228.8 ± 43*** |
| IMM-H007 | 7 | 100 mg/kg | 236.0 ± 9.3** | 256.3 ± 46.4 |
| IMM-H007 | 7 | 200 mg/kg | 228.5 ± 13.2*** | 250.2 ± 27.8 |

Figure 5:
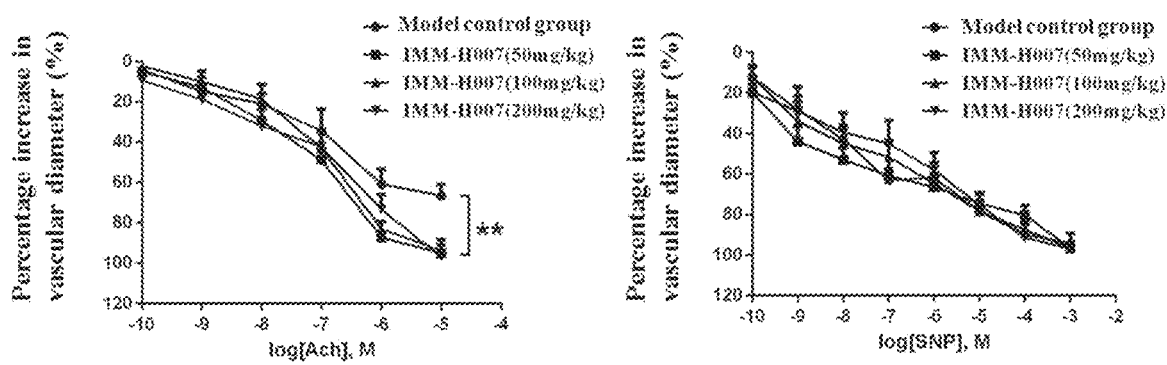
FIG. 5 illustrates effect of IMM-H007 on mesenteric microvascular endothelial function in ApoE−/− mice.

*$P < 0.05$,
**$P < 0.01$,
***$P < 0.001$ compared with model control group (3) Effect of IMM-H007 on Mesenteric Microvascular Endothelial Function in ApoE−/− Mice The results showed that after pre-administration of 2 μM phenylephrine for pre-contraction of blood vessels, vasodilatation response induced by different concentrations of ($10^{-10}$ to $10^{-5}$M) acetylcholine can evaluate the effect of drugs on vascular endothelial function. Compared with the model control group, the IMM-H007 administration 50 mg/kg dose group could significantly improve microvascular endothelial dysfunction caused by high fat without affecting blood lipid levels; the administration of IMM-H007 at a dose of 100 mg/kg could significantly improve the acetylcholine-induced endothelium-dependent relaxation response and improve the endothelial dysfunction without affecting cholesterol, triglyceride, low-density lipoprotein cholesterol or high-density lipoprotein cholesterol. The results showed that IMM-H007 could improve microvascular endothelial dysfunction independently of its lipid-lowering effect (results are shown in Tables 5 and 6 and FIG. 5).

TABLE 5

Effect of IMM-H007 on acetylcholine-induced endothelium-dependent relaxation of microvascular in ApoE−/− mice

| Groups | Model control group | IMM-H007 50 mg/kg | IMM-H007 100 mg/kg | IMM-H007 200 mg/kg |
|---|---|---|---|---|
| $1 \times 10^{-10}$ M Ach | 4.2 ± 2.3 | 5.0 ± 5.1 | 2.37 ± 3.4 | 9.5 ± 12.0 |
| $1 \times 10^{-9}$ M Ach | 15.0 ± 10.0 | 12.9 ± 12.6 | 10.2 ± 12.0 | 18.8 ± 17.5 |
| $1 \times 10^{-8}$ M Ach | 21.0 ± 1 1.8 | 29.3 ± 21.8 | 18.6 ± 17.2 | 32.0 ± 20.1 |
| $1 \times 10^{-7}$ M Ach | 34.4 ± 25.9 | 48.7 ± 12.8 | 43.1 ± 21.8 | 42.2 ± 20.8 |
| $1 \times 10^{-6}$ M Ach | 60.8 ± 18.2 | 87.3 ± 5.0** | 82.9 ± 8.5** | 73.3 ± 17.5* |
| $1 \times 10^{-5}$ M Ach | 66.5 ± 13.7 | 95.0 ± 4.4** | 93.9 ± 12.9** | 96.9 ± 14.2** |

*$P < 0.05$,
**$P < 0.01$ compared with model control group

TABLE 6

Effect of IMM-H007 on sodium nitroprusside endothelium-independent relaxation of microvascular in ApoE−/− mice

| Groups | Model control group | IMM-H007 50 mg/kg | IMM-H007 100 mg/kg | IMM-H007 200 mg/kg |
|---|---|---|---|---|
| $1 \times 10^{-10}$ M SNP | 12.1 ± 11.4 | 19.9 ± 10.1 | 11.9 ± 13.5 | 19.4 ± 3.05 |
| $1 \times 10^{-9}$ M SNP | 28.1 ± 15.7 | 43.9 ± 18.2 | 33.9 ± 23.5 | 28.9 ± 29.5 |
| $1 \times 10^{-8}$ M SNP | 42.9 ± 15.8 | 52.9 ± 14.2 | 44.9 ± 21.9 | 39.4 ± 24.2 |
| $1 \times 10^{-7}$ M SNP | 62.9 ± 42.6 | 60.9 ± 8.5 | 51.5 ± 17.9 | 44.9 ± 27.8 |
| $1 \times 10^{-6}$ M SNP | 61.9 ± 18.2 | 66.4 ± 11.6 | 64.6 ± 12.2 | 58.0 ± 21.3 |

TABLE 6-continued

Effect of IMM-H007 on sodium nitroprusside endothelium-independent relaxation of microvascular in ApoE-/- mice

| Groups | Model control group | IMM-H007 50 mg/kg | IMM-H007 100 mg/kg | IMM-H007 200 mg/kg |
|---|---|---|---|---|
| $1 \times 10^{-5}$ M SNP | 78.4 ± 11.9 | 74.5 ± 12.8 | 78.4 ± 13.0 | 75.3 ± 12.6 |
| $1 \times 10^{-4}$ M SNP | 89.8 ± 12.4 | 80.3 ± 12.1 | 87.5 ± 10.9 | 91.3 ± 6.2 |
| $1 \times 10^{-3}$ M SNP | 94.2 ± 12.2 | 96.5 ± 6.3 | 96.5 ± 3.6 | 96.9 ± 2.9 |

Figure 6:
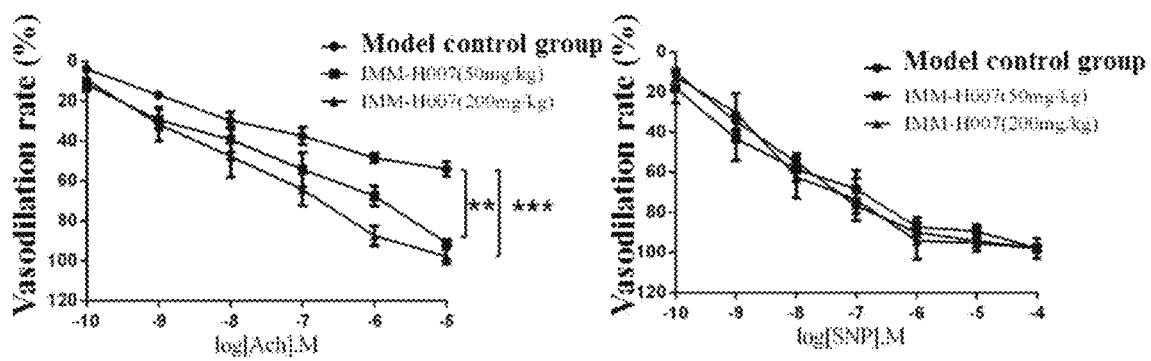
FIG. 6 illustrates effect of IMM-H007 on aortic vascular endothelial function in ApoE−/− Mice.

(4) Effect of IMM-H007 on Endothelial Function of Thoracic Aorta in ApoE-/- Mice The results showed that after pre-administration of 1 μM phenylephrine for pre-contraction of blood vessels, the vasodilatation response induced by different concentrations of ($10^{-10}$ to $10^{-5}$ M) acetylcholine can evaluate the effect of drugs on vascular endothelial function. Compared with the model control group, the IMM-H007 administration 50 mg/kg dose group could significantly improve the acetylcholine endothelium-dependent relaxation of aortic caused by high fat and improve endothelial dysfunction without affecting blood lipid levels, indicating that IMM-H007 can improve vascular endothelial dysfunction independently of its lipid-lowering effect (results are shown in Tables 7 and 8 and FIG. 6).

TABLE 7

Effect of IMM-H007 on acetylcholine endothelium-dependent relaxation of aortic vessel in ApoE-mice

| Groups | Model control group | IMM-H007 50 mg/kg | IMM-H007 200 mg/kg |
|---|---|---|---|
| $1 \times 10^{-10}$ M Ach | 3.82 ± 0.65 | 11.6 ± 7.0 | 9.4 ± 3.9 |
| $1 \times 10^{-9}$ M Ach | 16.8 ± 2.8 | 29.3 ± 11.2 | 31.4 ± 18.5 |
| $1 \times 10^{-8}$ M Ach | 29.6 ± 8.9 | 39.2 ± 14.0 | 47.6 ± 22.5 |
| $1 \times 10^{-7}$ M Ach | 37.3 ± 9.7 | 54.1 ± 18.8* | 64.2 ± 17.7** |
| $1 \times 10^{-6}$ M Ach | 48.4 ± 5.2 | 67.5 ± 11.0** | 87.4 ± 10.9*** |
| $1 \times 10^{-5}$ M Ach | 54.0 ± 8.0 | 91.0 ± 2.3*** | 97.8 ± 8.2*** |

*P < 0.05,
**P < 0.01,
***P < 0.001 compared with model control group

TABLE 8

Effect of IMM-H007 on sodium nitroprusside endothelium-independent relaxation of aortic vessel in ApoE-/- Mice

| Groups | Model control group | IMM-H007 50 mg/kg | IMM-H007 200 mg/kg |
|---|---|---|---|
| $1 \times 10^{-10}$ M SNP | 10.2 ± 1.5 | 18.0 ± 16.3 | 12.4 ± 8.4 |
| $1 \times 10^{-9}$ M SNP | 34.4 ± 8.5 | 43.1 ± 24.6 | 30.5 ± 20.8 |

TABLE 8-continued

Effect of IMM-H007 on sodium nitroprusside endothelium-independent relaxation of aortic vessel in ApoE-/- Mice

| Groups | Model control group | IMM-H007 50 mg/kg | IMM-H007 200 mg/kg |
|---|---|---|---|
| $1 \times 10^{-8}$ M SNP | 54.8 ± 9.1 | 58.4 ± 13.8 | 62.3 ± 22.7 |
| $1 \times 10^{-7}$ M SNP | 76.6 ± 7.8 | 68.3 ± 20.5 | 73.6 ± 23.3 |
| $1 \times 10^{-6}$ M SNP | 89.3 ± 5.1 | 87.2 ± 10.1 | 94.1 ± 20.6 |
| $1 \times 10^{-5}$ M SNP | 94.3 ± 5.8 | 89.4 ± 6.8 | 95.4 ± 8.5 |
| $1 \times 10^{-4}$ M SNP | 97.8 ± 4.0 | 97.8 ± 4.9 | 97.9 ± 10.8 |

(5) IMM-H007 Improves Endothelial Function Through the AMPK-eNOS Pathway

Figure 7:
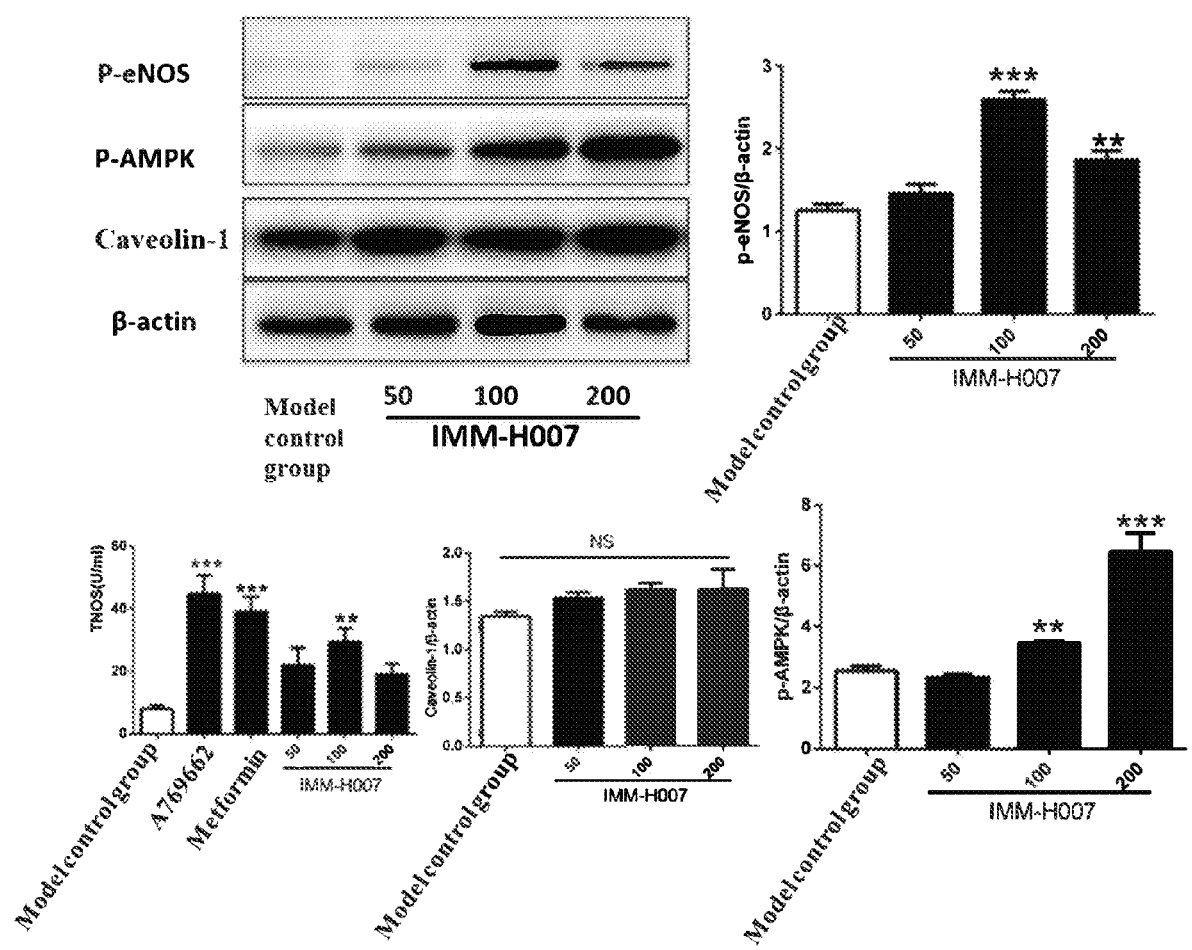
FIG. 7 illustrates that IMM-H007 improves endothelial function through the AMPK-eNOS pathway.

The expression levels of AMPK, pAMPK, peNOS, eNOS, Caveolin-1 proteins were analyzed and measured by Western Blotting to determine the total nitric oxide synthase activity in serum. The possible mechanism of IMM-H007 in improving endothelial function independent of hypolipidemic effect was analyzed. The experimental findings: IMM-H007 mainly through the activation of AMPK-eNOS pathway, improves the activity of nitric oxide synthase, increases NO production and improves blood vessel function (results are shown in FIG. 7).

(6) IMM-H007 Reduces Plaque Area in ApoE-/- Mice

Figure 8:
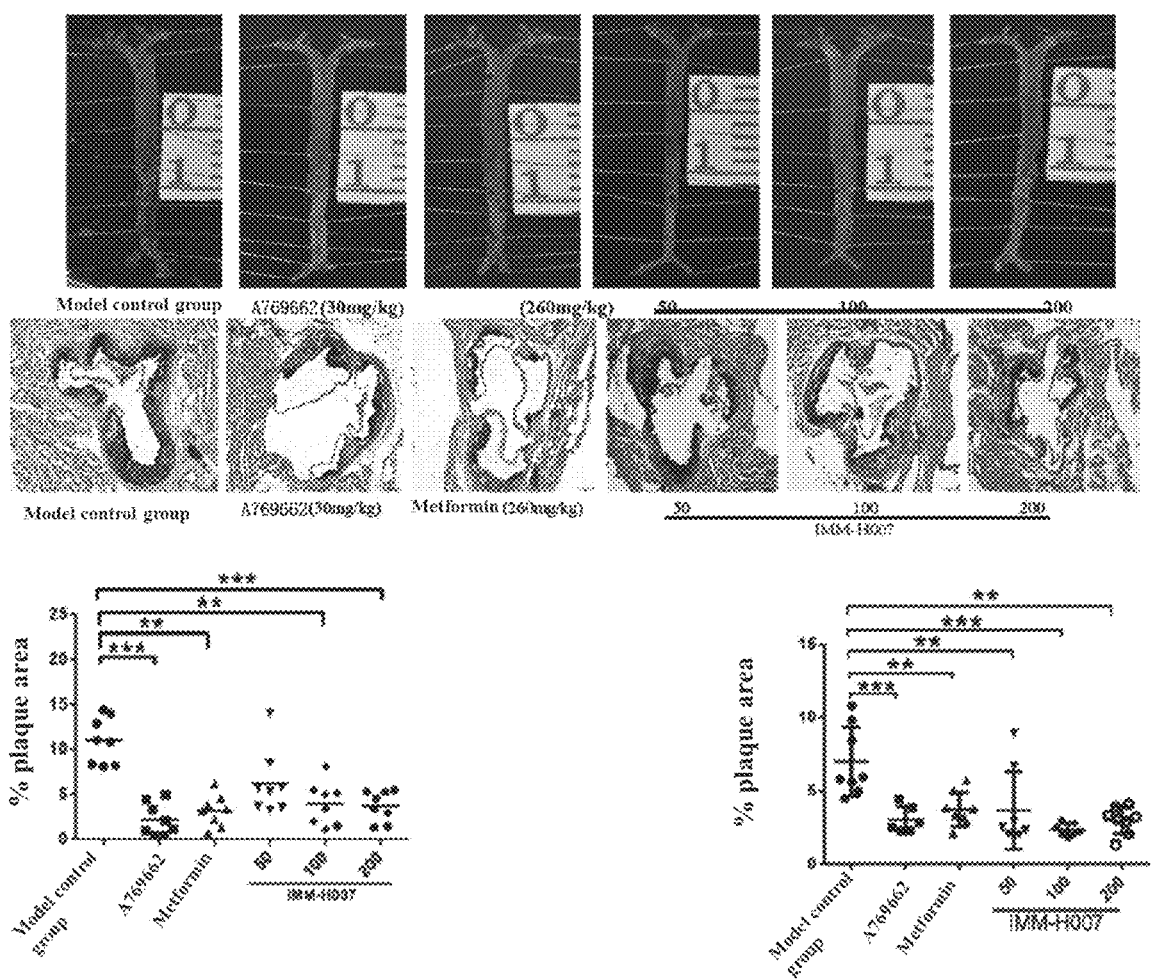
FIG. 8 illustrates that IMM-H007 reduces arterial plaque in ApoE−/− mice.

The elevated level of AMPK-eNOS protein and the improvement of vascular endothelial dysfunction are beneficial to alleviate the occurrence and development of atherosclerosis. In this study, atherosclerotic model ApoE-/- mice were given high-fat diet for 10 weeks to observe the plaque accumulation in the overall length of aorta and root of the artery, and then to observe the effect of IMM-H007 on atherosclerosis. The experimental results showed that: IMM-1007 could significantly reduce the plaque accumulation in the arch of aorta and overall length of aorta, and section staining of the root of aorta revealed a decrease in lipid accumulation at the plaque site, suggesting that IMM-H007 improves endothelial dysfunction to alleviate the progression of atherosclerosis (results are shown in Table 9 and FIG. 8).

TABLE 9

IMM-H007 reduces plaque area in the overall length of aorta and the root of aorta

| Groups | N | Dose | Overall length of aorta | Frozen section of root of aorta % |
|---|---|---|---|---|
| Model control group | 8 | — | 10.94 ± 2.60 | 7.00 ± 2.38 |
| A769662 | 8 | 30 mg/kg, ip | 2.61 ± 1.80 | 3.02 ± 0.89*** |
| Metformin | 8 | 260 mg/kg | 3.13 ± 1.76** | 3.73 ± 1.15** |
| IMM-H007 | 8 | 50 mg/kg | 6.18 ± 3.57 | 3.66 ± 2.65** |

TABLE 9-continued

IMM-H007 reduces plaque area in the overall length of aorta and the root of aorta

| Groups | N | Dose | Overall length of aorta | Frozen section of root of aorta % |
|---|---|---|---|---|
| IMM-H007 | 8 | 100 mg/kg | 3.93 ± 2.40** | 2.36 ± 0.43*** |
| IMM-H007 | 8 | 200 mg/kg | 3.67 ± 1.69*** | 2.97 ± 0.92** |

*P < 0.05,
**P < 0.01,
***P < 0.001 compared with model control group

Example 3 2',3,' 5'-triacetyl-N'(3-hydroxyphenyl) adenosine (IMM-H007) Improves Vascular Endothelial Function in Ob/Ob Obese Mice Experimental Materials and Instruments IMM-H007 (independently developed by the Institute of Materia Medica, Chinese Academy of Medical Sciences), sodium carboxymethyl cellulose (Sinopharm Chemical Reagent Co., Ltd.), sodium chloride, potassium chloride, magnesium sulfate, sodium bicarbonate, glucose, EDTA, and acetylcholine (sigma), sodium nitroprusside (VETEC), R-(-) phenylephrine (J&K Scientific LTD.), Triglyceride Assay Kit, Total Cholesterol Assay Kit, High-Density Lipoprotein Cholesterol Assay Kit, and Low-Density Lipoprotein Cholesterol Assay Kit (BioSino Bio-Technology & Science Inc.), and Free Fatty Acid Assay Kit (Sekisui Medical Technology LTD.); insulin, glucose, Roche Blood Glucose Test Paper, analytical balance, Olympus SZ51 stereomicroscope, shaker, stapler, Pressure Myography System-120CP, fine microsurgery tweezer, fine microsurgical scissor, 95% $O_2$ and 5% $CO_2$ mixture, and surgical operation silicone disk.

Animals and Experimental Design

Ob/Ob obese mice (male, 4 weeks old) were purchased from the Model Animal Research Center of Nanjing University.

After 1 week of adaptive feeding, animals were randomly divided into two groups according to body weight: model control group, and IMM-H007 group (400 mg/kg), 10 in each group, and were given normal feed and simultaneously administered intragastrically at a dose of 0.1 ml/10 g body weight, and were continuously administered and fed for 9 weeks. The changes of food intake and body weight were recorded, and routine biochemical indicators such as blood lipids and blood glucose, etc. were measured. After 9 weeks, 3 animals were taken from each group and the mesenteric arterioles were taken for measurement of vascular endothelial function in the same manner as in Example 2.

Detection Indicators (1) Routine Biochemical Indicators and (2) Vascular Endothelial Function Data Statistics Experimental results were expressed as mean X±SD. A t-student test was performed using Graphpad Prism software. Differences between groups were analyzed by one way-ANOVA parameter analysis or non-parametric LSD-t method. P<0.05 indicated statistical difference, and P<0.01 indicated significant difference.

Experimental Results

Figure 9:
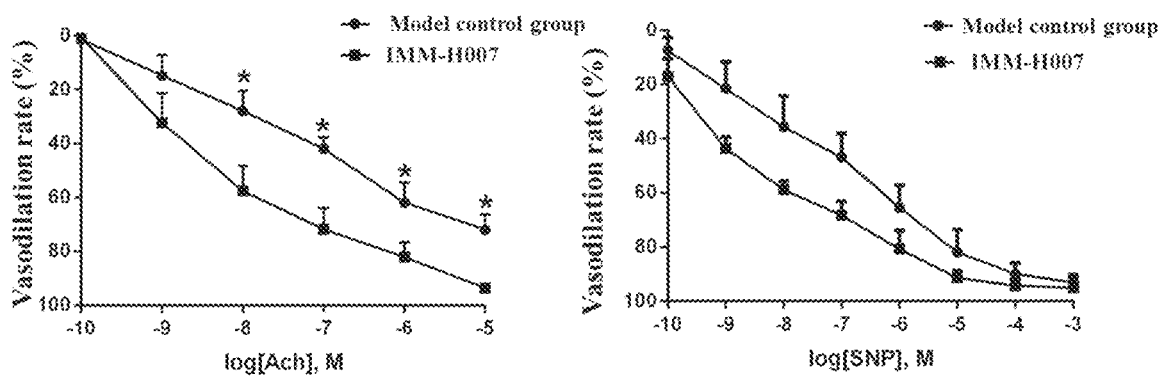
FIG. 9 illustrates that IMM-H007 improves microvascular endothelial function in Ob/Ob obese mice.

The results showed that after the Ob/Ob obese mice were fed with normal feed for 9 weeks, the detection of blood glucose and insulin levels indicated that an insulin resistance model was formed, and the insulin resistance is an important cause of endothelial function disorders, therefore, we determined the microvascular endothelial function in 9-week Ob/Ob mice. The study found that: IMM-H007 (400 mg/kg) dose group could improve microvascular endothelial function (experimental results shown in Tables 10, 11 and 12 and FIG. 9).

TABLE 10

Effect of IMM-H007 on Biochemical Indexes in Ob/Ob Obese Mice

| | Model group (n = 10) | | IMM-H007 400 mg/kg (n = 10) | |
|---|---|---|---|---|
| Variable | 4 week | 9 week | 4 week | 9 week |
| Body weight (g) | 46.61 ± 0.48 | 55.74 ± 0.58 | 44 44 ± 0.50* | 51.18 ± 0.67*** |
| Ingestion (g/day) | 5.59 ± 0.15 | 5.97 ± 0.21 | 5.48 ± 0.05 | 5.47 ± 0.08* |
| Fasting blood glucose (mmol/l) | 5.95 ± 0.20 | 10.02 ± 0.93 | 6.69 ± 0.12 | 9.98 ± 0.51 |
| Fasting insulin (ng/ml) | 3.18 ± 0.28 | 7.74 ± 0.58 | 1.60 ± 0.18*** | 6.07 ± 0.48* |
| Triglyceride (mmol/l) | 0.76 ± 0.04 | 0.91 ± 0.07 | 0.69 ± 0.03 | 0.52 ± 0.09** |
| Free fatty acid (mEq/l) | 1.24 ± 0.06 | 0.91 ± 0.04 | 1.06 ± 0.03* | 0.44 ± 0.07*** |
| Total cholesterol (mmol/l) | 3.80 ± 0.12 | 6.31 ± 0.23 | 3.57 ± 0.07 | 4.13 ± 0.67** |
| Low-density lipoprotein (mmol/l) | 1.18 ± 0.05 | 2.57 ± 0.11 | 1.16 ± 0.04 | 1.70 ± 0.28** |

*P < 0.05,
**P < 0.001 compared with model group

TABLE 11

Effect of IMM-H007 on acetylcholine endothelium-dependent relaxation of microvascular in Ob/Ob obese mice

| Groups | Model control group | IMM-H007 400 mg/kg |
|---|---|---|
| $1 \times 10^{-10}$ M Ach | 1.44 ± 0.9 | 0.96 ± 0.85 |
| $1 \times 10^{-9}$ M Ach | 14.79 ± 13.2 | 32.3 ± 18.9 |
| $1 \times 10^{-8}$ M Ach | 27.9 ± 12.7 | 57.6 ± 15.8* |
| $1 \times 10^{-7}$ M Ach | 41.9 ± 7.1 | 71.7 ± 13.5* |

TABLE 11-continued

Effect of IMM-H007 on acetylcholine endothelium-dependent relaxation of microvascular in Ob/Ob obese mice

| Groups | Model control group | IMM-H007 400 mg/kg |
|---|---|---|
| $1 \times 10^{-6}$ M Ach | 61.9 ± 12.8 | 82.1 ± 9.3* |
| $1 \times 10^{-5}$ M Ach | 71.9 ± 9.7 | 93.6 ± 1.1* |

*$P < 0.05$ compared with model control group

TABLE 12

Effect of IMM-H007 on sodium nitroprusside endothelium-independent relaxation of microvascular in Ob/Ob obese mice

| Groups | Model control group | IMM-H007 100 mg/kg |
|---|---|---|
| $1 \times 10^{-10}$ M SNP | 7.45 ± 8.2 | 16.9 ± 6.3 |
| $1 \times 10^{-9}$ M SNP | 21.6 ± 17.1 | 43.5 ± 4.1 |
| $1 \times 10^{-8}$ M SNP | 36.6 ± 19.7 | 58.9 ± 3.2 |
| $1 \times 10^{-7}$ M SNP | 46.8 ± 15.1 | 68.3 ± 5.1 |
| $1 \times 10^{-6}$ M SNP | 65.4 ± 14.3 | 80.8 ± 6.9 |
| $1 \times 10^{-5}$ M SNP | 81.9 ± 14.3 | 91.4 ± 2.5 |
| $1 \times 10^{-4}$ M SNP | 89.8 ± 6.8 | 94.3 ± 2.3 |
| $1 \times 10^{-3}$ M SNP | 93.1 ± 4.9 | 95.0 ± 3.8 |

The invention claimed is:

1. A method of treating and/or alleviating vascular inflammation in a host in need thereof comprising administering from 50 mg/kg to 200 mg/kg of 2',3',5'-triacetyl-$N^6$ (3-hydroxyphenyl) adenosine of formula (I)

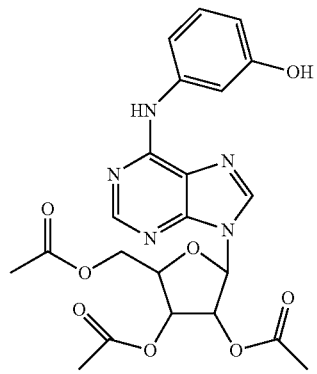

(I)

to a person, and wherein the treatment results in a decrease in TNF-α and/or VCAM-1 serum inflammatory factors in the person being treated.

2. The method of claim 1, further comprising wherein the triacetyl-3-hydroxyl phenyl adenosine of formula (I) is incorporated into a pharmaceutical composition by mixing with a pharmaceutically acceptable carrier or excipient prior to the administering step.

3. The method of claim 2, wherein the form of the pharmaceutical composition is selected from the group consisting of a tablet, a capsule, a pill, and an injectable liquid.

4. The method of claim 2, wherein the form of the pharmaceutical composition is selected from the group consisting of a sustained-release preparation, a controlled-release preparation, and a microparticle delivery system.

5. The method of claim 1, wherein the vascular inflammation comprises acute vascular inflammation or chronic vascular inflammation.

* * * * *